United States Patent [19]

Furuichi et al.

[11] 4,340,971
[45] Jul. 20, 1982

[54] DENTAL RADIOGRAPHIC APPARATUS FOR PHOTOGRAPHING ENTIRE JAWS

[75] Inventors: Shuhei Furuichi, Shiga, Japan; Masakazu Suzuki, Naka, both of Japan

[73] Assignee: Kabushiki Kaisha Morita Seisakusho, Kyoto, Japan

[21] Appl. No.: 188,884

[22] Filed: Sep. 19, 1980

[30] Foreign Application Priority Data

Sep. 20, 1979 [JP] Japan .................................. 54-121524

[51] Int. Cl.³ .............................................. G03B 41/16
[52] U.S. Cl. ......................................... 378/40; 378/91
[58] Field of Search .................................. 250/439 P

[56] References Cited
U.S. PATENT DOCUMENTS 4,039,837  8/1977  Ohta ................................ 250/439 P Primary Examiner—Craig E. Church
Attorney, Agent, or Firm—Koda and Androlia

[57] ABSTRACT

The disclosure relates to a dental radiographic apparatus for photographing the entire jaws having a rotary arm including an X-ray generator disposed in an opposed relation with an X-ray film feed means. The apparatus includes a means for detecting electrically the shape and characteristics of an object through the position of the rotary arm rotated and a means for automatically controlling the rotation speed of the arm and the feed speed of an X-ray film in response to the detection signal generated by the electrical detection means, whereby it is intended to provide a clear and sharp X-ray photographic image free from distortion, uniform in density and optional in rate of enlargement.

7 Claims, 13 Drawing Figures

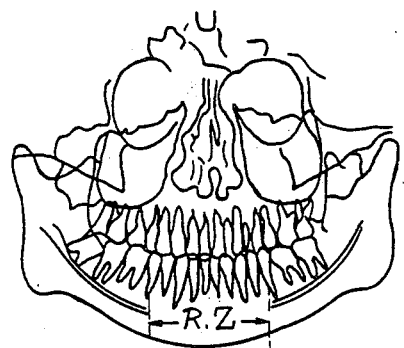
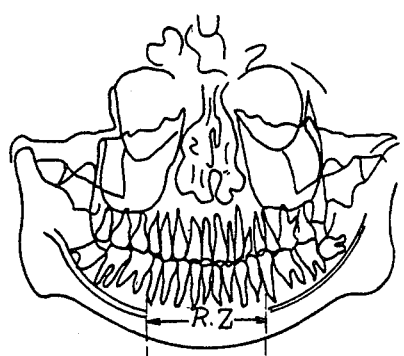
Fig. 10
Fig. 10
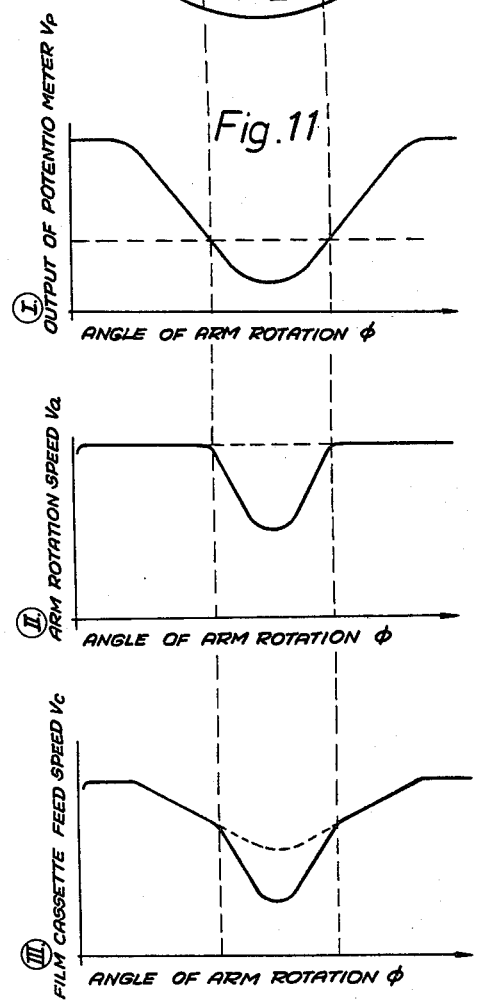
Fig. 11
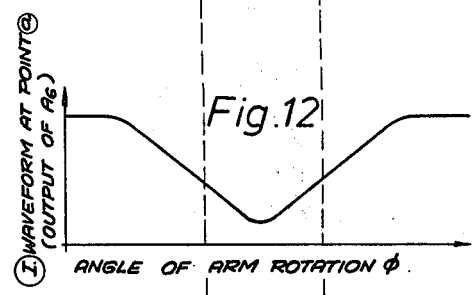
Fig. 12
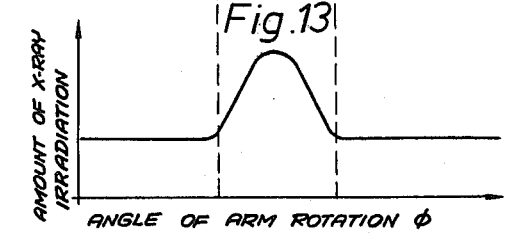
Fig. 13

DENTAL RADIOGRAPHIC APPARATUS FOR PHOTOGRAPHING ENTIRE JAWS

BACKGROUND OF THE INVENTION

1. Field of the Invention

This invention relates to a dental radiographic apparatus, and more particularly to a dental radiographic apparatus for an entire jaw having a rotary arm comprising means for detecting the shape of the object and means for controlling the rotation speed of the arm and the feeding speed of X-ray film.

2. Prior Art

Medical examination made by use of tomography of a curved plane has been playing a very important role in dental treatment in recent years, and the fact that an X-ray photographic image obtained by this photography is clear and sharp and free from distortions makes it indispensable for exact treatment free from a mistaken diagnosis.

But the conventional radiographic apparatuses for photographing the entire jaws, of the type described above, are usually nothing but proposals for a photographic apparatus which can embody the theoretically elucidated tomography of a curved plane into a practical form. For example, mostly apparatuses constructed so as to obtain a desired panoramic X-ray photograph by controlling the amount of X-rays irradiated upon an object by synchronously changing the rotatingly moving speed of an X-ray generator and the feed speed of an X-ray film by arrangement of mechanically connected parts in the apparatus, so to speak, apparatuses designed to make synchronous control fo the moving speed of the X-ray generator and the feed speed of X-ray film and intended primarily to elucidate tomography of a curved plane in relation with the principle of the tomography.

In the apparatuses of the type described above, despite the fact that they have rendered it possible to make practical use of a panormaic X-ray photograph of the entire jaws by tomography of a curved plane, limited characteristic traits of the mechanical structure thereof have made it difficult to prevent distortions and provide uniform density in the resulting picture. Accordingly, when a tomographic picture of a curved plane was taken by controlling the feed speed of film in synchronism with the rotation speed of the rotary arm, it was difficult or next to impossible to prevent distortions of the image and lack of unformity in density in the picture obtained, and especially in the X-ray photographic image of the front tooth region, it was impossible to prevent not only lack of sharpness of the image caused by shortage of density in the X-ray photographic image due to the presence of the cervical vertebrae but also to nonuniformity in a rate of enlargement of the individual tooth images in the dental arch.

SUMMARY OF THE INVENTION

This invention has been completed after an intense study and effort to remove the disadvantages of the conventional type panormaic dental radiographic apparatus for photographing the entire jaws and to obtain a panoramic X-ray photograph superior in quality and has for its ultimate object the provision of an apparatus useful for dental treatment by which a dentist is enabled to make exact diagnosis.

The present inventors previously completed an invention concerning an X-ray film feed control system in a dental radiographic apparatus for photographing the entire jaws wherein a motor in charge of feeding an X-ray film is provided independently of a motor in charge of rotating a horizontal rotary arm and the feed speed of the X-ray film is controlled independently of the rotation speed of the rotary arm. The present invention relates to improvements in the previous invention, and is intended to obtain a panoramic X-ray photographic image of the entire jaws by changing also the rotation speed of a horizontal rotary arm in response to the position of the arm rotated. Accordingly, the invention offers the following advantages.

1. Improvments in the efficiency of panormaic X-ray photographing of the entire jaws:

Highly efficient control of the amount of X-ray irradiation is made possible by controlling both the feed speed of an X-ray film and the rotation speed of a horizontal rotary arm because the invention has rendered it possible to control not only the feed speed of X-ray film but also the drive speed of a motor in charge of rotation of the arm in response to the position of the arm rotated.

2. X-ray photographic image made clear and sharp:

An X-ray photographic image uniform in density can be obtained by controlling the rotation speed of the rotary arm rotatingly travelling along the dental arch of an object, changing the feed speed of X-ray film by an electrical means synchronously with or independently of the rotation speed of the arm, and suitably controlling the amount of X-rays irradiated upon the dental arch of the object. Especially, control of the feed speed of X-ray film independently of the rotation speed of the arm provides a clear and sharp X-ray photographic image uniform in density and free from effects of the presence of the cervical vertebrae also in photographing the front tooth region.

3. X-ray photographing image made optional in rate of enlargement:

The rate of longitudinal enlargement of an object image in a panoramic X-ray photograph is determined by relative position (particularly relative distance) in relation to an X-ray source, an object and an X-ray film, and the rate of lateral enlargement is determined by the above three and film feed speed. Accordingly, independent control of the relative position of the above three with respect to one another or of the film feed speed and arm rotation speed provides an X-ray photographic image uniform in rate of enlargement, and in addition, a more effective X-ray photographic image in which a desired portion of the dental arch is optionally increased in the rate of enlargement over the other portions thereof, with the result that a dentist is not only enabled to guard himself from wrong diagnosis but can positively make exact diagnosis with ease.

A description will now be given of a preferred embodiment of the invention shown by way of example with reference to the accompanying drawings.

BRIEF DESCRIPTION OF THE DRAWINGS

FIG. 10 schematically shows a panoramic X-ray photograph of the entire jaws;

FIG. 11 shows potentiometer output VP, arm rotating speed va, and film cassette feed speed vc, respectively corresponding to parts of the X-ray photographic image in FIG. 10;

FIG. 12 shows a performance waveform chart at point a, point 4 and point b in FIGS. 8 and 9; and FIG. 13 shows an amount of X-rays irradiated in the use of the invention.

DETAILED DESCRIPTION OF THE INVENTION

Referring to an embodiment of the invention with reference to FIGS. 1 to 6 of the drawings, the apparatus employs a system of changing the resistance value of a variable resistor and detecting an electrical signal necessary for control by using a mechanical means as a means of continuously and discontinuously detecting the position of X-rays of X-ray generator irradiated on the dental arch of an object in response to the rotational movement of a horizontal rotary arm rotating round the object. Details of the system will later be described.

Figure 1:
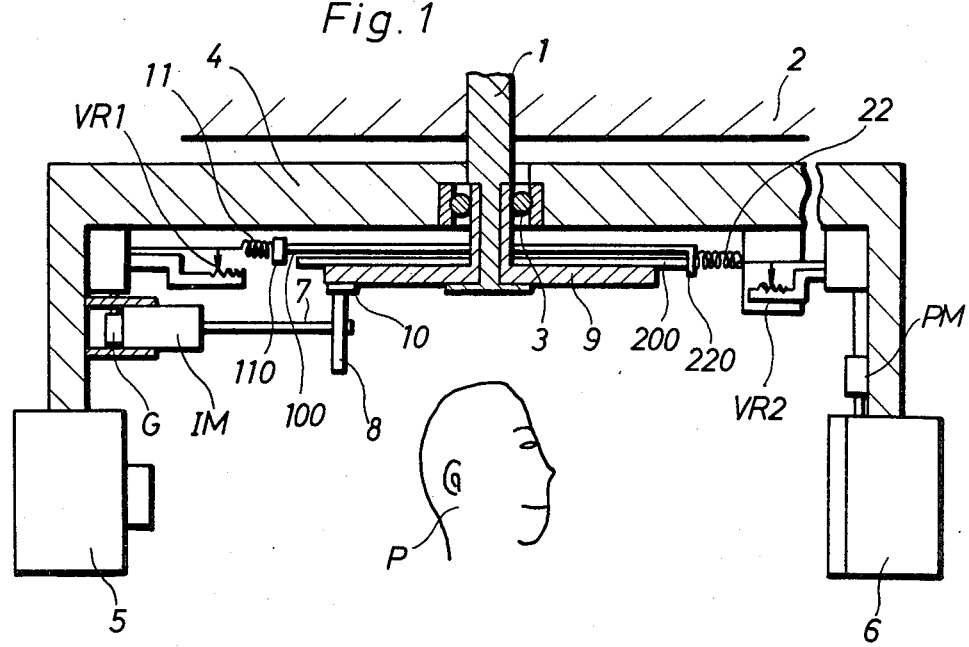
FIG. 1 is a longitudinal sectional side view of one embodiment of a radiographic apparatus for taking a panoramic photograph of the entire jaws according to the invention.
Figure 2:
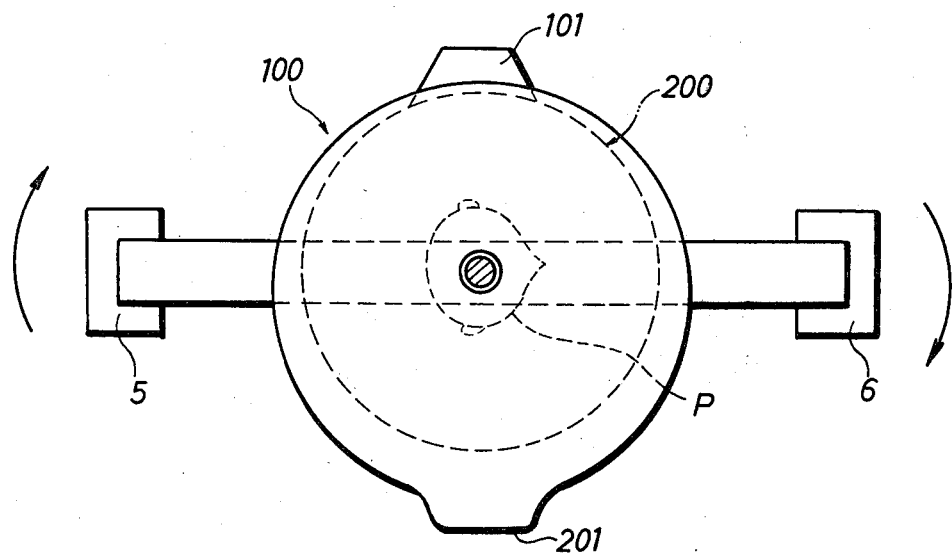
FIG. 2 is a plan view showing a relationship between the center of rotation of the rotary arm and the cam plate in FIG. 1.
Figure 3:
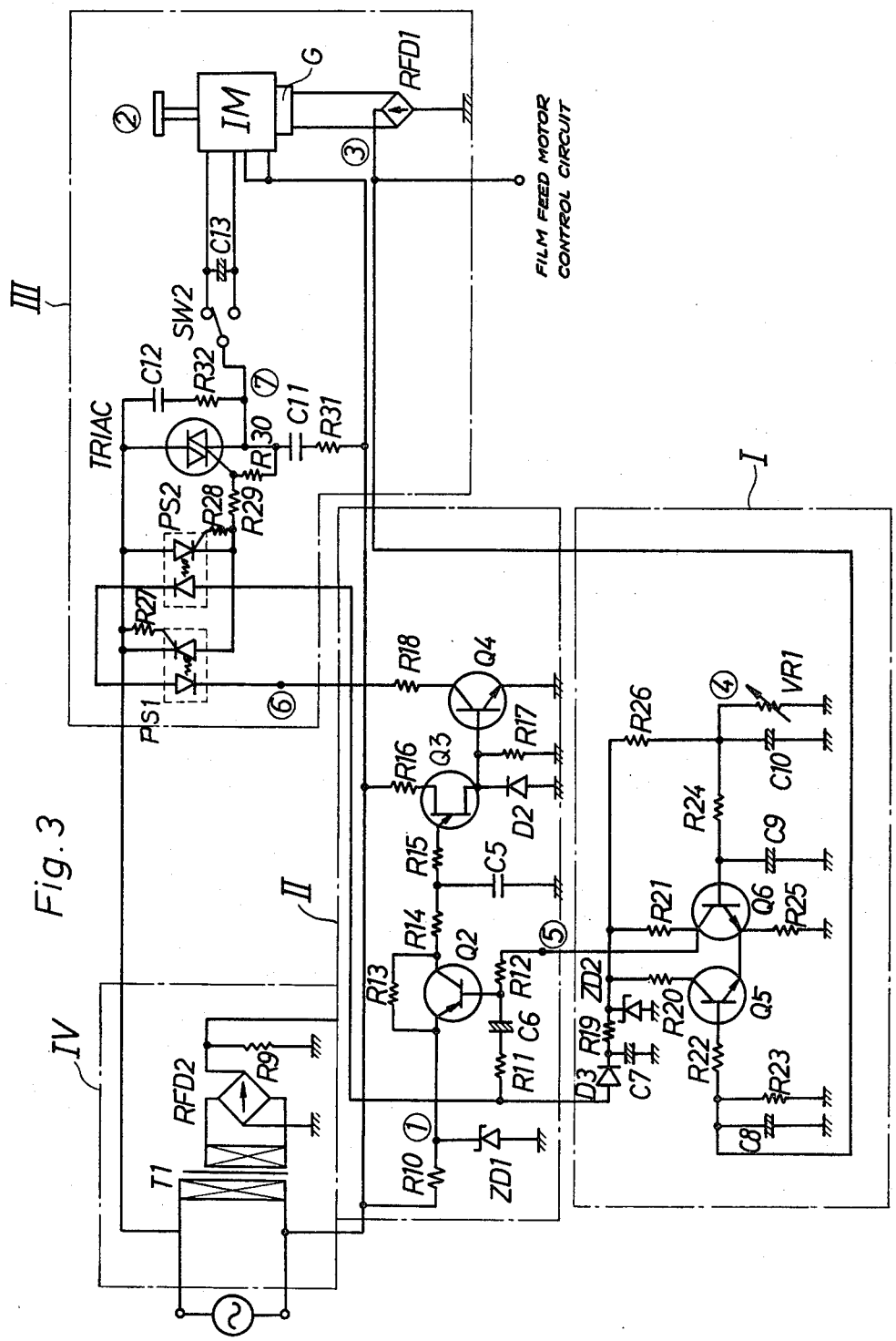
FIG. 3 is a drive motor speed control circuit for the rotary arm constituting the essential parts of the apparatus.
Figure 5:
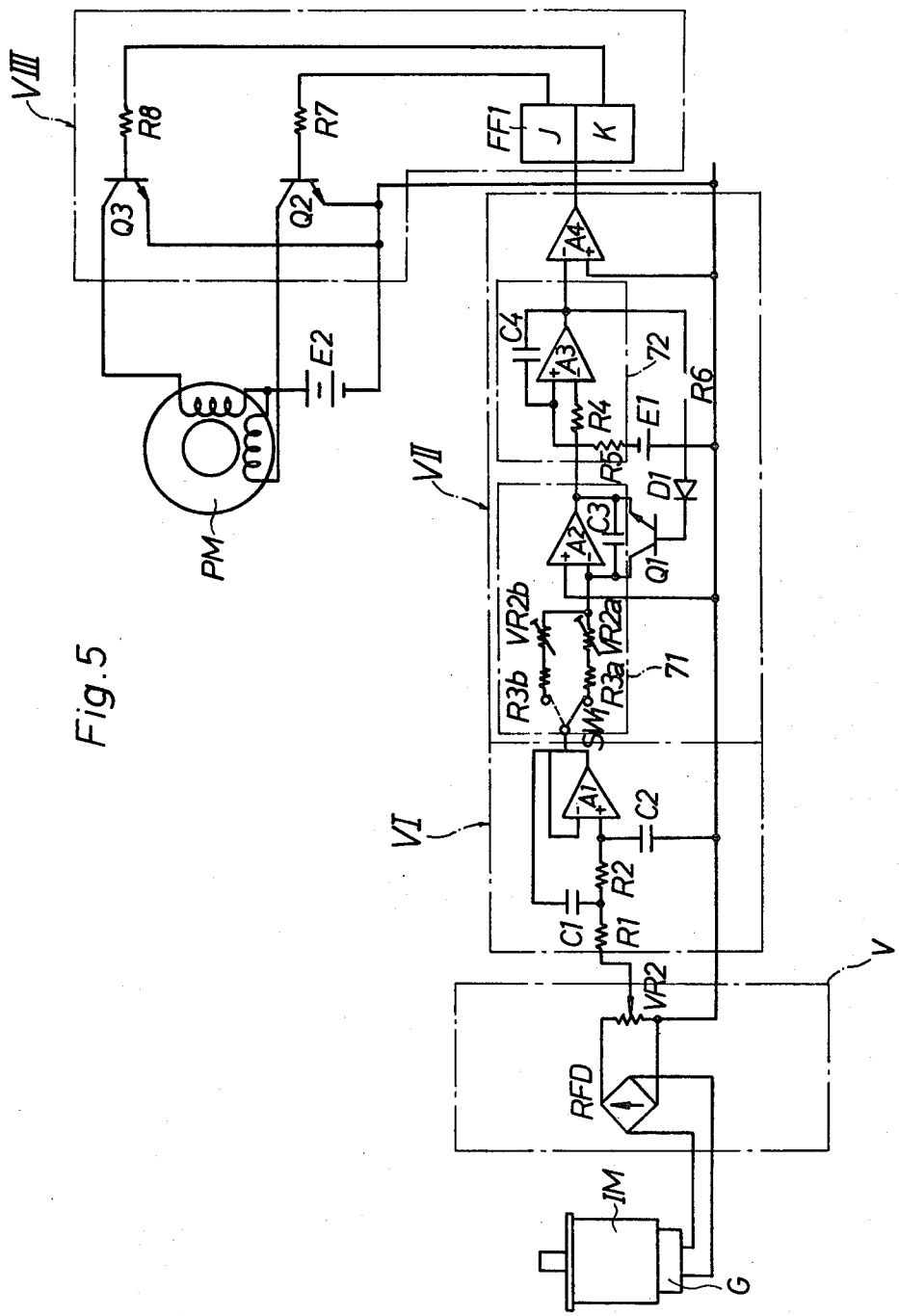
FIG. 5 is a circuit diagram for bringing film feed speed into synchronism with drive motor for rotating arm and controlling the speed of film feed motor.

Referring now to the structure of the dental radiographic apparatus for photographing the entire jaws, the numeral 1 in FIGS. 1 and 2 designates a base shaft suspended from a support base 2 and a horizontal rotary arm 4 (hereinafter referred to as a rotary arm) is suspended through a bearing 3 on the base shaft 1 so as to permit the free horizontal rotation thereof. An X-ray generator 5 is held at one end of the arm 4 and an X-ray film cassette holder 6 is held at the other end thereof at an angle phase of 180° in an opposed relation with respect to the generator. In time of photographing, the arm rotatingly travels within the same plane area in which the generator 5 and the cassette holder 6 having an object P disposed therebetween surrounds the object P in such a manner that the feeding of an X-ray film (not shown) is effected in the film holder 6 in synchronism with the rotatingly travelling speed of the arm. The arm is integrally provided with an induction motor IM (referred to hereinafter as a motor IM) for rotatingly moving the rotary arm 4 and also provided on the output shaft 7 of the motor IM with a pinion 8, while the base shaft 1 is fixedly mounted with a receiving plate 9. On the underside of the plate 9 is fixed a rack 10 circumferentially around the base shaft 1. The pinion and the rack are mated with each other, and the rotary arm 4 is forced to rotate in accordance with the rotation of the pinion 8 on the rack 10 by rotation of the motor IM. Furthermore, the rotary arm 4 is mounted with a pulse motor PM for feeding the X-ray film. These two motors IM and PM are connected to each other by a synchronous circuit whose detailed circuit is shown in FIG. 5 and the speed of motor PM is synchronously varied in proportion to the speed of rotation of the motor IM, namely the travelling speed of the rotary arm 4 and the rotation speed of X-ray generator 5 and the feed of X-ray film is controlled by the synchronous change in the rotation speed of the motor PM. The numerals 100 and 200 designate cam plates placed detachably on the top of the receiving plate. The cam plates depress plungers 110 and 220 respectively by rotation of the rotary arm 4, which depression, in turn, changes the resistance value of variable resistors VR1 and VR2. By this change in the value of the variable resistors is changed the rotation speed of the pulse motor synchronously with or independently of the motor IM. The detailed circuitry of motor IM is shown in FIG. 3, while the detailed circuitry of motor PM is shown in FIG. 5. The cam plates 100 and 200 includes circumferential cam faces respectively eccentric with respect to the base shaft 1 and are of special configuration having protrudent portions 101 and 201 respectively flat at the ends in a mutually opposed relation in a part of the plates. It is to be understood that the cam plates are not only of such configuration but may also be of any other configurations which provide a speed control of cam plates optimum to making a tomogram of a curved plane is relation to the object P. And a description of the use of a panoramic X-ray photographing apparatus for photographing the entire jaws is dispensed with, since it is not an object of the invention.

Referring now to the speed control of the drive motor for rotary arm IM (to be referred to hereinafter as a motor IM), an electric circuit diagram for such speed control, for example, as apparent from FIG. 3, includes a speed deviation detection circuit unit I, a trigger pulse generation circuit unit II, a speed control circuit unit III, and a power supply circuit unit IV. The outline of the operating principle of these circuits is to change an oscillation period of the trigger pulse generated in an oscillation period preset by the trigger pulse generation circuit II and to thereby control the rotation speed of motor IM through the phase control made by a triac. Stated more concretely, the principle is to compare the set voltage, which is determined by the variable resistor VR1 being changed by rotation of the arm 4, with the output voltage of tachogenerator connected to the motor IM through the speed deviation detection circuit unit I and to control the rotation speed of motor IM by quickening the generation period of trigger pulse generated by the trigger pulse generation circuit unit II when the set voltage is higher than the output voltage of tachogenerator and making phase control of alternating current supply voltage applied to triac of speed control circuit unit III by the trigger pulse.

As described, the set voltage is set by changing the resistance value of variable resistor VR1 by moving the plunger 110 depressed by rotation of the rotary arm 4 (an electrical signal necessary for control is produced in response to the position of the arm 4 rotated. The tachogenerator G is constructed to the motor IM and is constructed to produce output proportional to the rotation speed of the motor IM.

Figure 4:
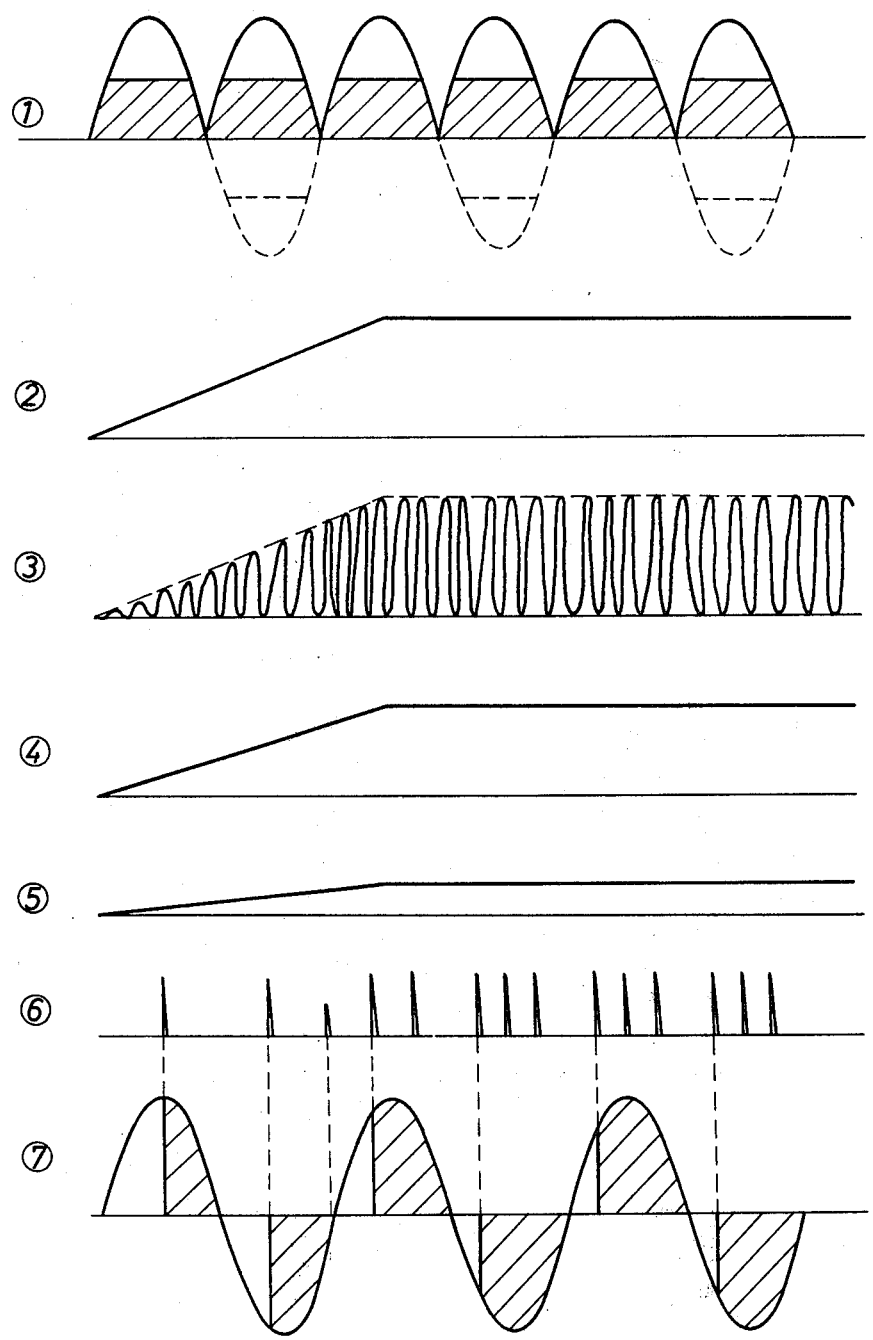
FIG. 4 is a performance waveform chart of each element in FIG. 3.

In the description to be given hereinafter, a change in the rotation speed of motor IM is shown for clarity of explanation is substantially trapezoid as shown in FIG. 4(2), but it should be understood that, in practical application, speed control optimum to the tomography of a curved plane may be effected by selecting suitably the shape of the cam plate 100 in accordance with the configuration of an object P. In FIG. 3, the reference character G designates a tachogenerator directly connected to the output shaft of drive motor IM for rotating the arm 4, the tachogenerator causing AC voltage (not shown) in proportion to the number of rotations of the motor IM. The character RFD1 designates a rectifier for changing the AC voltage into a pulsating current. The character T−1 designates a power transformer having a bridge rectifier RFD2 connected to the secondary side thereof, and AC supply voltage (not shown) is converted into a pulsating current clipped by Zenor diode ZD1 as shown in FIG. 3. The plunger 110 is depressed by rotation of the rotary arm 4 in accordance with the aforestated cam plates, and speed setting of the circuit in FIG. 3 is determined as shown in FIG. 4(2) by a variable resistor VR1 changed and set by the plunger thus depressed, and the deviation of output of the speed setting of the circuit of FIG. 3 from the pulsating current (FIG. 4(3)) obtained by the output of the tachogenerator G connected to the motor IM is amplified (FIG. 4(5)) and is introduced to the trigger pulse generation circuit unit II, and a trigger pulse (FIG. 4(6)) is generated in response to this voltage differentiation and speed is controlled by phase control of triac through photothyristors PS1 and PS2. It will be understood that, in case the set voltage (FIG. 4(4)) is increased over the output of the generator G (FIG. 4(3)) when the set point of variable resistor VR1 is changed or the speed of the motor IM is changed, the output of transistor Q6 is increased to thereby increase the base current of transistor Q2 and to quicken the charging of a trigger pulse generation capacitor G5, shorten the period of pulse generation to quicken the ignition of triac and increases the rotation speed of motor IM and increases the rotation of motor IM to the set point specified by variable resistor VR1 (see FIGS. 4 through 7).

Next, a description will be given of the principle in which the pulse motor PM for feeding film is controlled in speed synchronously with or independently of the rotation speed of motor IM, with reference to FIGS. 5 and 6. In this case, an electric circuit comprises, as for example shown in FIG. 5, a number-of-rotation ratio setting circuit unit V, a low-pass filter circuit unit VI, a voltage control pulse oscillation circuit unit VII, and a pulse motor driving circuit VIII, and the outline of the operating principle of the circuit units is to control a film feed speed synchronously with or independently of the motor IM by changing the resistance value of variable resistor VR2 by the plunger 220 depressed by rotation of the rotary arm 4, dividing the voltage fed through the generator G connected to the motor IM by the change of resistance value thus effected, (dividing the voltage supplied and making the divided voltage into an electrical signal necessary for control in response to the position of the arm rotated) removing the high-frequency component from the divided voltage through the low-pass filter circuit unit VI and thereafter inputting the high-frequency component into the voltage control pulse oscillation circuit unit VII, and driving the film feed pulse motor PM by the pulse fed by the circuit VII.

A description will now be given in greater detail of the operating principle of the electric circuit in FIG. 5 with reference to the performance waveform chart in FIG. 6. In FIG. 5, the character VR2 designates a variable resistor which changes and sets the number of rotations (rotation speed) of motor IM, namely X-ray film feed speed with respect to the rotatingly travelling speed of X-ray generator 6, and the value of this variable resistor is set at a desired value before X-ray photographing is started. A circuit including capacitors C1 and C2, resistors R1 and R2 and amplifier A1 constitutes a low-pass phase filter circuit V1 and is designed to eliminate the high-frequency component (noise) contained in the aforestated pulsating current (FIG. 6(3)). The voltage control pulse oscillation circuit unit VII containing a Miller circuit, a comparison circuit and a buffer amplifier A4 is a V-F conversion circuit which generates pulse voltage by a frequency proportional to the output voltage of the low-pass circuit unit VI and converts the pulse voltage into a trigger pulse and functions to operate flip-flop FF1 in the subsequent stage. Transistors Q2 and Q3 constitute a motor drive circuit unit VIII for pulse motor PM, and resistors R7 and R8 indicate base resistors of transistors Q2 and Q3 respectively. A resistance series connector of resistors R3a and variable resistor VR2a and a resistance series connector of resistor R3b and variable resistor VR2b are constructed to be selected by switch SW1 in the voltage control pulse oscillation circuit unit VII. This selection is intended to select a conversion factor of the voltage control pulse oscillation unit VII, and, stated concretely, the selection is intended to determine a time constant of the Miller integration circuit constructed to include amplifier A2 by a CR circuit between the selected resistance series connectors and a capacitor C3. The selection of the resistance series connectors is made before starting of X-ray photographing in the same manner as setting of resistance value of the variable resistor VR1. A comparison circuit 72 compares a reference voltage source E1 with this integration output by comparator A3 and includes resistors R4 and R5 and a capacitor Cr.

Figure 6:
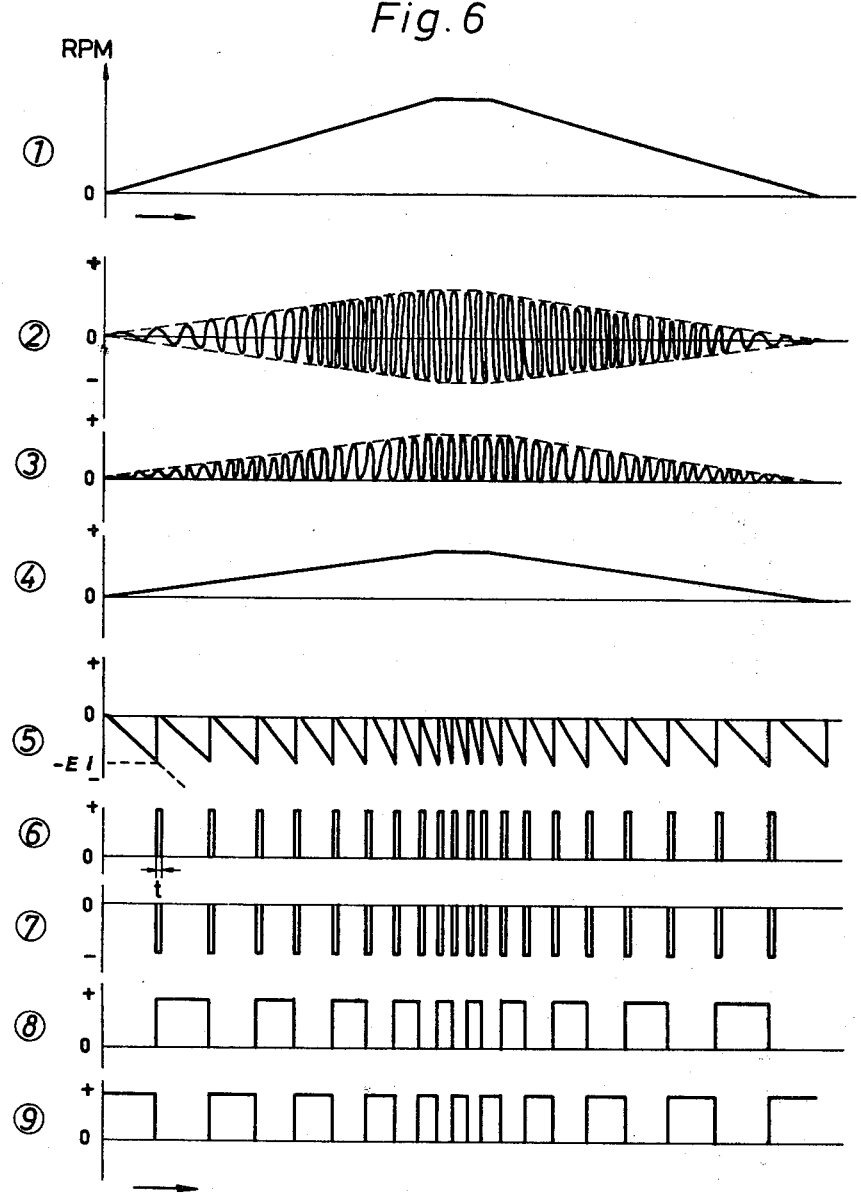
FIG. 6 is a performance waveform chart of each element in FIG. 5.

Referring now to the operation of the electric circuit in FIG. 5 in conjunction with the performance waveform chart in FIG. 6, the drive motor IM for the rotary arm is actuated and then the arm is rotated with the object P placed between the arm and the tachogenerator. When the arm changes rotation speed in response to its position of rotation as shown in FIG. 6(1), (in this case, for convenience of explanation, a change in the speed of rotation of the motor IM is shown in a trapezoidal form, but it should be understood that in an actual case of application, if the cam plates are formed in any optional form in conjunction with the object P in the same manner as the aforesaid speed control of the drive motor for the rotary arm, a change in speed optimum to the tomograph of a curved plane is shown) the tachogenerator G connected to the motor IM outputs a speed electromotive force proportional to the number of rotations of the motor IM as shown in FIG. 6(2), and this electromotive force is converted into a pulsating current (FIG. 6(3)) by a full-wave rectifying circuit RFD1 and thereafter passes from a variable resistor VR2 through a low-pass filter circuit unit VI to thereby have a noise component attenuated and eliminated into a DC voltage proportional to the number of rotations of motor as shown in FIG. 6(4).

At this time, the pulsating current voltage (FIG. 6(3)) passing from the full-wave rectifying circuit through the low-pass filter circuit unit VI, when it passes through a variable resistor VR2, is subjected to a change in voltage by the resistance value set by variable resistor VR2, and the DC voltage in FIG. 6(4) appearing in the form of output of the low-pass filter circuit unit VI is increased or decreased in response to the resistance value of the variable resistor VR2. The output of the low-pass filter circuit unit VI is inputted through the resistor R3a and variable resistor VR2a or the resistor R3b and variable resistor VR2b selected by a switch SW1 into an amplifier A2 and is integrated by the amplifier, and generates a saw tooth wave (FIG. 6(5)) of frequency proportional to the above output voltage. At the same time, comparison is made by comparator A3 between Miller integration circuit output voltage and reference voltage source E1, and when integration output exceeds reference voltage, the comparator A2 outputs positive output voltage and this voltage is fed back to the Miller integration circuit through a resistor R6 and a diode D1, and a transistor Q1 is biased and energized to short-circuit a capacitor C3. Then, the Miller integration circuit output voltage is instantaneously reduced to zero (FIG. 6(5)). The output voltage of comparator A2 is held at the same voltage for a certain time t by the time constant determined by capacitor C4 and resistor R5, transistor Q1 is de-energized and intergration operation is again started. A positive pulse synchronous with such a saw tooth wave as shown in FIG. 6(6) is outputted from the comparator A3 by such repeated operation, and the positive pulse is introduced into a buffer amplifier A4 where the positive pulse is reversed, and flip-flop FF1 is triggered by the output of the buffer amplifier (FIG. 6(7)). The flip-flop FF1 alternately generates the pulse voltage shown in FIG. 6(8) (9) each time it is triggered by the output of the buffer amplifier (FIG. 6(7)) and energizes the transistors Q2 and Q3 of pulse motor drive circuit unit VIII alternately by the pulse voltage to thereby drive a pulse motor PM by the drive power source E2 for the motor and to turn the motor PM and feed an X-ray film. The intervals at which the buffer amplifier driving the flip-flop FF1 at this time outputs a pulse are synchronized with the saw tooth wave (FIG. 6(5)) generated by the Miller integration circuit 71 and accordingly, the pulse intervals are proportional to the number of rotations of the motor IM and in consequence, the pulse recurrence rate (FIG. 6(8) (9)) which the flip-flop FF1 triggered through the output of the buffer amplifier outputs is also brought into proportion to the number of rotations of the motor IM, with the result that the motor PM is rotated in synchronism with the motor IM.

Figure 7:
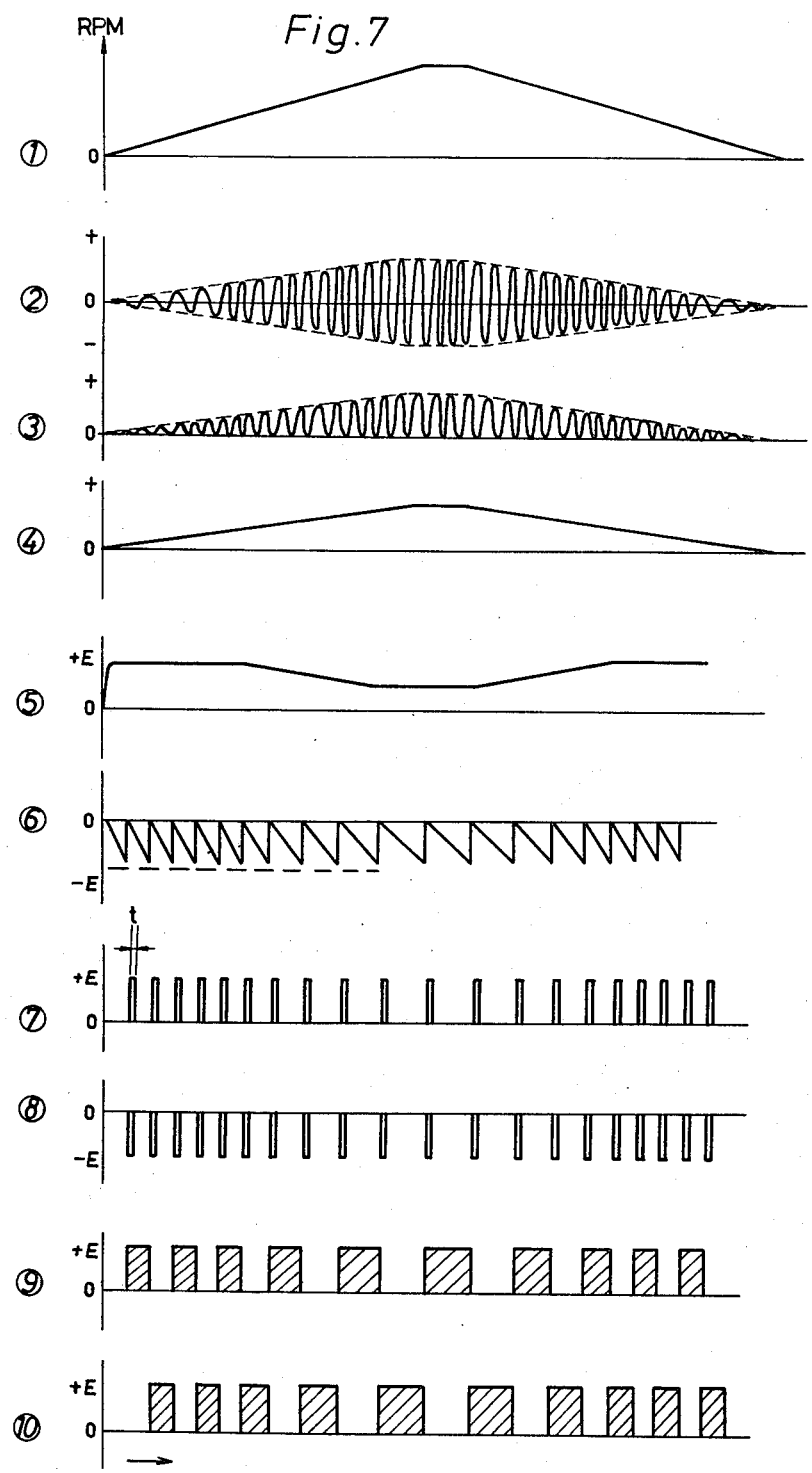
FIG. 7 is a performance waveform chart in the case of the film feed motor speed being controlled by the shape of a cam plate independently of the drive motor for rotating the rotary arm.

Now, a description will be given of the principle on which the X-ray film feed motor is controlled in speed independently of the rotation speed of the rotary arm drive motor by the number-of-rotations ratio setting signal generated in response to the position of the arm rotated. The electric circuit for this purpose is the same as shown in FIG. 5 and can be provided by changing the variable resistor VR2 of the number-of-rotations ratio setting circuit unit V. FIGS. 7(1) through (4) are performance waveform charts respectively corresponding to FIGS. 6(1) through (4) and FIG. 7(5) shows a change in set voltage generated by variable resistor VR2 in accordance with the rotation of the rotary arm. It will be readily understood from FIG. 7, in the same manner as in the case of the aforesaid synchronous control, that because the change in set voltage shows the value decreased in the middle stage of control in response to the rotation of the arm, the rotation speed of X-ray film feed motor is gradually decreased in the middle stage of control.

A description will now be given of the case wherein cam plates for controlling the rotation speed of the rotary arm are enabled to be used in combination with a part of a cam plate for controlling film cassette feed, namely, the case wherein the rotation speed of the arm and feed speed of the film cassette can be controlled by the use of one cam plate.

Figure 8:
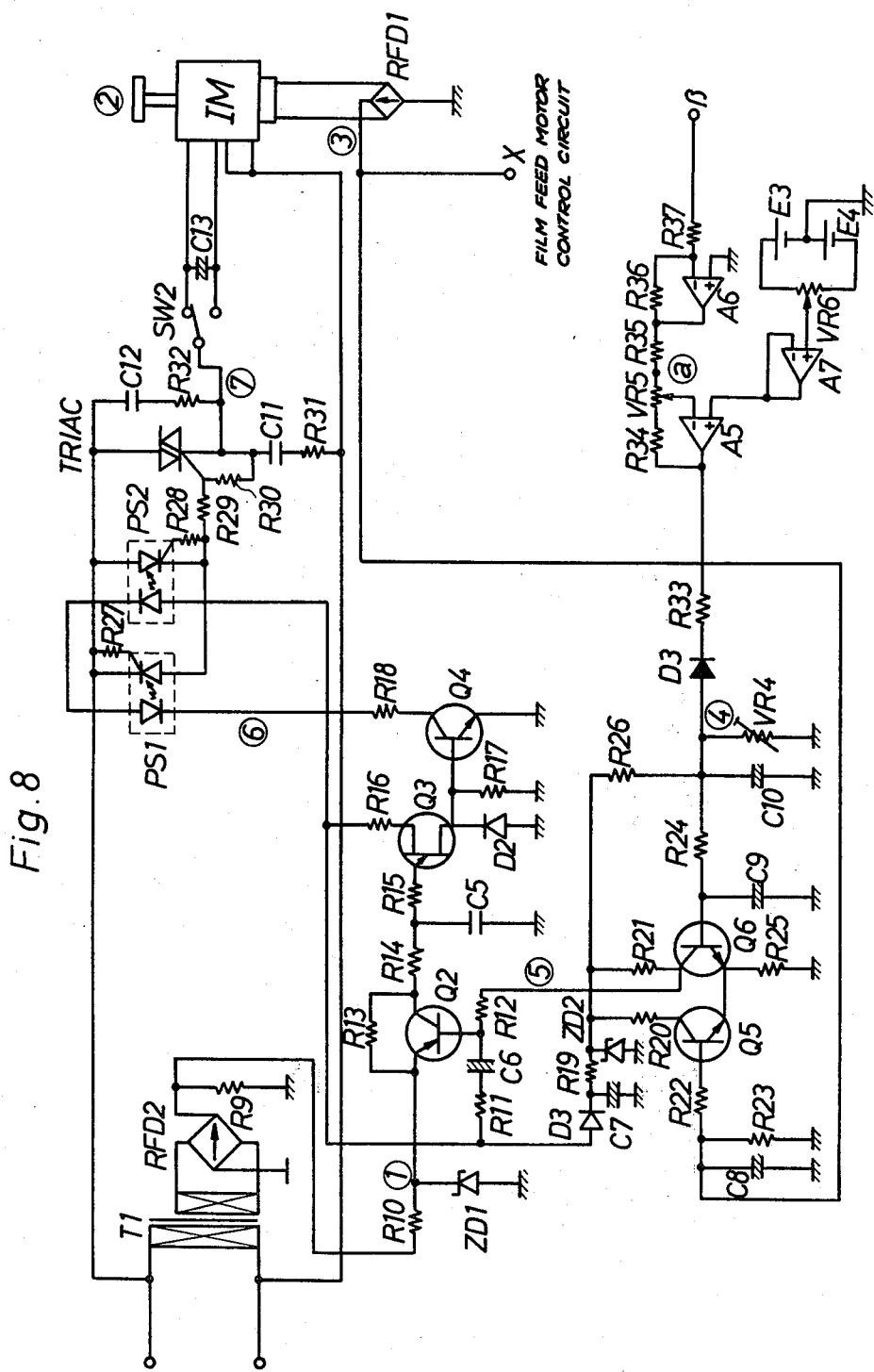
FIG. 8 is a circuit for controlling rotation speed of rotary arm in the case of controlling both the rotation speed of arm and the speed of film feed motor by use of one cam plate.
Figure 9:
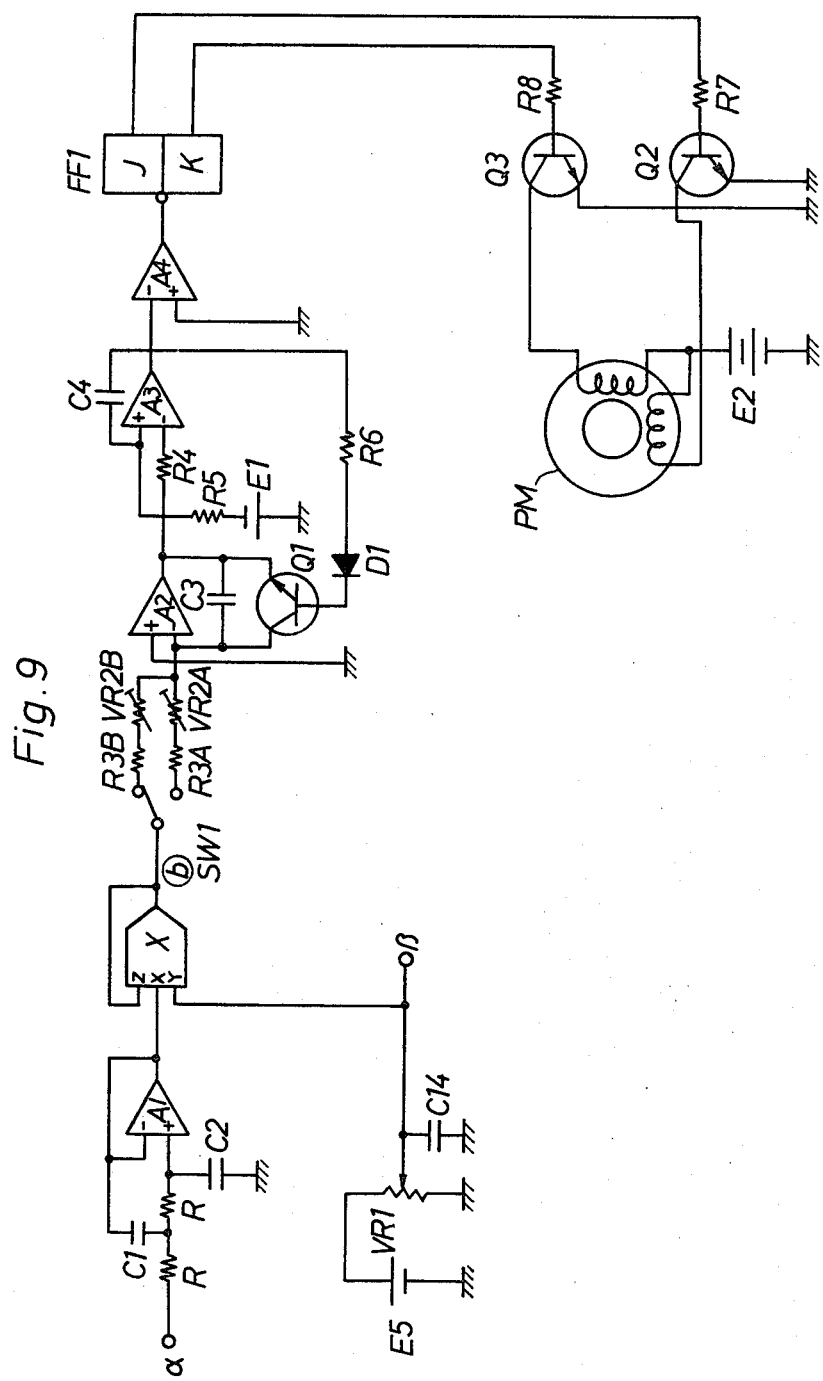
FIG. 9 is a circuit diagram for controlling the speed of film feed motor in FIG. 8.

FIG. 8 shows another embodiment of a circuit for controlling the speed of the drive motor for the rotary arm. FIG. 9 shows another embodiment of a circuit for controlling the speed of a film cassette feed motor. FIG. 10 is a schematic diagram showing a panoramic photographic image of the entire jaws. And FIGS. 11 and 12 show performance diagrams in the portions corresponding to the photographic images in FIG. 10 used in the control circuits in FIGS. 8 and 9.

The control circuit in FIG. 8 is designed in such a manner that an amplifier circuit comprising an operational amplifier A5 and a bias circuit are added in parallel to capacitor C10 with respect to the circuit in FIG. 3 and that, only when the output of the operational amplifier A5 is reduced below the potential across the capacitor C5, the potential across the capacitor C10 is controlled by the output voltage of the operational amplifier through diode D3. The control circuit in FIG. 9 controls the output voltage that rectifies, amplifies and smoothes the output voltage of operational amplifier A1, namely, the output of tachometer connected to the arm drive motor by dispensing with the variable resistor VR2 of FIG. 5, locating instead a multiplier behind the operational amplifier A1, and introducing divided voltage output responsive to the resistance value of potentiometer VR1 into the multiplier. FIG. 11(1) shows voltage at point $\beta$ in FIG. 9, namely, output corresponding to the resistance value of the potentiometer relative to the angle of rotation of the arm which is depressed on the cam plates, the voltage producing, in accordance with the rotation of the arm, the voltage that is determined by the shape of cam plate and the angle of rotation of the arm. As shown in FIG. 11(II), the drive motor for rotating the arm is actuated simultaneously with the starting of photographing and increases rotation to the number of rotations corresponding to the voltage set by variable resistor VR4 in FIG. 8 and continues rotating at constant speed up to a density rectification zone R.Z. (a point corresponding to the cervical vertebrae of an object). In the density rectification zone R.Z. of the front teeth region, the output voltage of potentiometer determined by the shape of cam plates and the angle of rotation of the arm is introduced into the operational amplifier A6, the output of operational amplifier is led to an operational amplifier A5, bias is imparted by PC-power sources E3 and E4, variable resistors VR6 and amplifier A7 to a reference level of the output voltage of the operational amplifier A5, and the gain of the amplifier A5 is adjusted by the variable resistor VR5 and the width area and amount of adjustment which adjusts the rotation speed of the arm are controlled as shown in FIGS. 12(I) and (II). The output of operational amplifier A6, as shown in FIG. 12(I), is lower in the density rectification zone of the front teeth than the set voltage of rotation speed of the arm regulated by variable resistor VR4, and as shown in FIG. 12(II), the rotation speed of the arm is controlled in the zone to a speed corresponding to the output voltage of operational amplifier A6. At the same time, the film cassette feed motor drives a film cassette at a speed proportional both to the drive motor for the arm and to the output of potentiometer as shown in FIG. 11(III) and FIG. 12(III), and irrespective of the amount of adjustment of rotation speed of the arm, controls the amount of X-rays the film receives by adjustment of rotation speed of the arm while the angle of rotation and the amount of film cassette feed are constantly maintained at a specified relation with each other and provides a photograph having uniform density and good contrast over the entire X-ray film surface.

As described above, the dental radiographic apparatus for photographing the entire jaws according to the invention makes it possible to provide an X-ray photographic image free from blurs and is capable of producing a desired rate of enlargement in the tomography of a curved plane by providing a motor for feeding an X-ray film independently of a drive motor for rotatingly moving a horizontal rotary arm, providing two means for generating an electrical signal in response to the position of the rotary arm rotated, controlling the number of rotations of the drive motor for rotating the arm by electrical signal detected by one of the detecting means, and controlling the rotation speed of the motor for feeding an X-ray film sny-the arm by the electrical signal detected by the other detecting means. Furthermore, stated differently, when X-ray photographing is effected of the front teeth of an object, the invention makes it possible not only to obtain an X-ray photographic image uniform in density by reducing the rotation speed of the film feed motor independently of the rotation speed of the rotary arm drive motor but also to obtain an X-ray photographic image having any desired rate of enlargement thereof by controlling the rotation speed of the film feed motor independently of the rotatingly travelling speed of the rotary arm.

It is to be understood that the mechanical structure and electric circuits shown in the embodiment of the invention are intended merely for illustration of preferred embodiments of the invention and that various modifications, additions and replacements concerning the mechanical structure and electric circuits are possible in relation to design within the scope of the invention without departing from the spirit thereof.

I claim:

1. A dental radiographic apparatus for photographing the entire jaws including a horizontal rotary arm and a drive motor for rotating said horizontal rotary arm, said arm having an X-ray generator disposed at one end thereof and having an X-ray film cassette holder disposed at the other end thereof in an opposed relation with each other and a motor for feeding X-ray film in said X-ray film cassette holder, said apparatus being characterized in that said apparatus comprises at least one circuit for detecting as an electrical signal the rotation position of said horizontal rotary arm, a circuit for controlling the speed of said drive motor, said circuit controlling the speed of the drive motor in response to the electrical signal detected by said detecting circuit, and a circuit for automatically controlling the speed of an X-ray film feed motor synchronously with or independently of the drive motor of said rotary arm.

2. A dental radiographic apparatus for photographing the entire jaws according to claim 1, wherein means for detecting as an electrical signal the rotation position of said horizontal rotary arm comprises a variable resistor whose resistance is varied by the rotation of said horizontal rotary arm.

3. A dental radiographic apparatus for photographing the entire jaws according to claim 1, wherein said circuit for controlling said film feed motor speed has as an input thereinto the rotational output of said drive motor and automatically controls the rotation speed of the film feed motor in synchronism with the drive motor.

4. A dental radiographic apparatus for photographing the entire jaws according to claim 1, wherein said means for detecting the position of said horizontal rotary arm comprises at least one cam plate depressing at least one plunger on a rotary plate provided on said horizontal rotary arm, said cam plate being fixed to a support shaft of the rotary arm and being designed not to rotate together with rotation of the arm, said plunger being located at a suitable point on the outer periphery of said rotary plate and being constructed so as to change the resistance value of at least one variable resistor through a spring in response to rotation of the horizontal rotary arm.

5. A dental radiographic apparatus for photographing the entire jaws according to claim 3, wherein said circuit for controlling the speed of said drive motor comprises a set speed deviation detection circuit unit and a speed control circuit unit, said detection circuit unit comparing the output voltage of a tachogenerator connected to the drive motor with said electrical signal corresponding to the rotation position of said arm and outputting the output difference between the electrical signal and the output signal as an electrical signal, said speed control unit controlling the rotational speed of said rotary arm drive motor by phase control of the motor in response to the output signal of said speed deviation detection circuit unit.

6. A dental radiographic apparatus for photographing the entire jaws according to claim 1, wherein said circuit for controlling the speed of said drive motor automatically controls the speed of rotation of said rotary arm drive motor in response to the electrical signal indicative of the rotation position of said arm.

7. A dental radiographic apparatus for photographing the entire jaws according to claim 4, wherein said circuit for controlling the speed of said drive motor comprises a tachogenerator connected to the drive motor which electrically converts the number of rotations of the drive motor into an electrical signal, a number of rotation ratio setting circuit unit for further converting the output of said tachogenerator into an electrical signal corresponding to the rotation position of the arm, a low-pass filter circuit unit for damping and eliminating a high-frequency component of the output of said setting circuit unit, a voltage control pulse oscillation circuit unit for converting the output voltage of said low-pass filter circuit unit into a pulse signal of frequency proportional thereto, and a pulse motor drive circuit for controlling the number of rotations of a pulse motor for feeding an X-ray film by said pulse signal generated.

* * * * *